US012718597B2

(12) United States Patent
Kim et al.

(10) Patent No.: US 12,718,597 B2
(45) Date of Patent: Aug. 25, 2026

(54) APPARATUS AND METHOD FOR VERTEBRAL BODY RECOGNITION IN MEDICAL IMAGES

(71) Applicant: CLARIPI INC., Seoul (KR)

(72) Inventors: Jong Hyo Kim, Seoul (KR); Chang Won Kim, Yongin-si (KR); Je Myoung Lee, Goyang-si (KR); Tae Jin Kim, Seoul (KR)

(73) Assignee: CLARIPI INC., Seoul (KR)

( * ) Notice: Subject to any disclaimer, the term of this patent is extended or adjusted under 35 U.S.C. 154(b) by 289 days.

(21) Appl. No.: 18/514,637

(22) Filed: Nov. 20, 2023

(65) Prior Publication Data

US 2024/0169745 A1 May 23, 2024

(30) Foreign Application Priority Data

Nov. 23, 2022 (KR) ........................ 10-2022-0158696

(51) Int. Cl.
*G06V 20/60* (2022.01)
*G06T 5/70* (2024.01)
(Continued)

(52) U.S. Cl.
CPC ................ *G06V 20/60* (2022.01); *G06T 5/70* (2024.01); *G06T 7/11* (2017.01); *G06T 15/10* (2013.01);
(Continued)

(58) Field of Classification Search
CPC ............................................ G06T 2207/30012
See application file for complete search history.

(56) References Cited

U.S. PATENT DOCUMENTS

2009/0245608 A1* 10/2009 Wan .......................... G06T 7/12 382/131
2009/0262998 A1* 10/2009 Wang ..................... G16H 30/40 382/131
(Continued)

FOREIGN PATENT DOCUMENTS

KR 10-2020-0073953 A 6/2020
KR 10-2022-0132146 A 9/2022

OTHER PUBLICATIONS

B. Cai et al., "Orthographic Pooling: Learned Maximum Intensity Projection for Vertebrae Labelling," 2022 44th Annual International Conference of the IEEE Engineering in Medicine & Biology Society (EMBC), Glasgow, Scotland, United Kingdom, 2022, pp. 2149-2152. (Year: 2022).*

(Continued)

*Primary Examiner* — Gandhi Thirugnanam

(57) ABSTRACT

The present disclosure provides an apparatus of identifying a vertebral body from a medical image, and the apparatus includes a vertebral bone identification module configured to identify the vertebral body based on a multi-slice medical image provided from an outside, in which the vertebral identification module reconstructs the multi-slice medical image to create a three-dimensional medical image, obtains a coronal projection image for the three-dimensional medical image by projecting the three-dimensional medical image in a coronal plane direction, divides the coronal projection image into a selection area including at least one of a lumbar and a thoracic, obtains area information corresponding to the selection area in the three-dimensional medical image based on the divided selection area, and performs numbering on the vertebral body based on the area information and the three-dimensional medical image.

18 Claims, 3 Drawing Sheets

(51) Int. Cl.
*G06T 7/11* (2017.01)
*G06T 15/10* (2011.01)
*G06V 10/77* (2022.01)
*G06V 20/50* (2022.01)
*G16H 30/40* (2018.01)

(52) U.S. Cl.
CPC .............. *G06V 10/77* (2022.01); *G06V 20/50* (2022.01); *G16H 30/40* (2018.01); *G06T 2207/10081* (2013.01); *G06T 2207/10088* (2013.01); *G06T 2207/10104* (2013.01); *G06T 2207/20021* (2013.01); *G06T 2207/20081* (2013.01); *G06T 2207/30012* (2013.01); *G06T 2210/12* (2013.01); *G06T 2210/41* (2013.01); *G06V 2201/033* (2022.01)

(56) References Cited

U.S. PATENT DOCUMENTS

| | | | | |
|---|---|---|---|---|
| 2010/0086185 | A1* | 4/2010 | Weiss | G16H 30/40<br>382/131 |
| 2012/0163687 | A1* | 6/2012 | Plakas | G06T 7/74<br>382/131 |
| 2021/0216822 | A1* | 7/2021 | Paik | G10L 15/22 |
| 2024/0169745 | A1* | 5/2024 | Kim | G06V 20/50 |
| 2024/0177836 | A1* | 5/2024 | Paik | A61B 5/742 |

OTHER PUBLICATIONS

De Leener et al., B. De Leener, S. Kadoury, J. Cohen-Adad, Robust, accurate and fast automatic segmentation of the spinal cord Neuroimage, 98 (2014), pp. 528-536 (Year: 2014).*

Sekuboyina, A., Rempfler, M., Valentinitsch, A., Menze, B. H. & Kirschke, J. S. Labeling vertebrae with two-dimensional reformations of multidetector Ct images: an adversarial approach for incorporating prior knowledge of spine anatomy. Radiol. Artif. Intell. 2, e190074 (2020). (Year: 2020).*

Sekuboyina, A. et al. Verse: A vertebrae labelling and segmentation benchmark for multi-detector Ct images. Med. Image Anal. 73, 102166 (2021). (Year: 2022).*

Glocker, B., Feulner, J., Criminisi, A., Haynor, D.R., Konukoglu, E. (2012). Automatic Localization and Identification of Vertebrae in Arbitrary Field-of-View CT Scans. Medical Image Computing and Computer-Assisted Intervention—MICCAI 2012. MICCAI 2012. Lecture Notes in Computer Science, vol. 7512. (Year: 2012).*

Sohee Park et al., "Deep Learning Algorithm for Reducing CT Slice Thickness: Effect on Reproducibility of Radiomic Features in Lung Cancer," Korean Journal of Radiology, 2019, pp. 1431-1440.

The Extended European Search Report for European Patent Application No. 23211412.4, dated Apr. 30, 2024.

Dejun Shi et al., "Automatic Localization and Segmentation of Vertebral Bodies in 3D CT Volumes with Deep Learning," International Symposium on Image Computing and Digital Medicine, Oct. 13, 2018.

Sohee Park et al., "Deep Learning Algorithm for Reducing CT Slice Thickness: Effect on Reproducibility of Radiomic Features in Lung Cancer," Korean Journal of Radiology, Jan. 1, 2019.

Taeyong Park et al., "Automated segmentation of the fractured vertebrae on CT and its applicability in a radiomics model to predict fracture malignancy," Scientific Reports, Apr. 25, 2022.

* cited by examiner

APPARATUS AND METHOD FOR VERTEBRAL BODY RECOGNITION IN MEDICAL IMAGES

CROSS REFERENCE TO RELATED APPLICATION

This application claims the benefit of Korean Patent Application No. 10-2022-0158696, filed on Nov. 23, 2022, the contents of which are all hereby incorporated by reference herein in their entirety.

BACKGROUND

Field

The present disclosure relates to an apparatus and method for vertebral body recognition in medical images, and more specifically, to a vertebral identification apparatus and a vertebral identification method for identifying a vertebral body in a medical image.

Related Art

In general, medical images acquired from a medical apparatus are used as a very important basis in modern medicine for decision-making by determining the presence or absence of lesions and characteristics thereof during the process of diagnosing and treating patients. For example, in the analysis of medical images taken of a spine, an interpreting doctor analyzes the images in order from an upper slice to a lower slice, and distinguishes between thoracic and lumbar.

However, recently, with the development of artificial intelligence (AI) technology, research and development on technology to distinguish the thoracic and lumbar from medical images using trained deep learning models is actively underway.

The conventional technology for identifying a vertebral body has already been described in "Korean Patent Publication No. 10-2020-0073953 (lumbar area analysis method in radiological images using artificial intelligence, and recording medium and method for performing the same, Jun. 24, 2020)". The disclosed invention is characterized by distinguishing the lumbar area based on the deep learning model that learned slice patterns.

However, the conventional deep learning research for vertebral body identification distinguishes the thoracic and lumbar based on a sagittal plane of a human body. However, when using the sagittal plane in the process of distinguishing the vertebrae into the thoracic and lumbar, it is difficult to identify the ribs, there is a possibility of errors occurring in the identification of the vertebral body. In particular, there is a problem that the possibility of error increases when performing identification in the sagittal plane direction depending on age and physical conditions of a patient.

SUMMARY

An object of the present disclosure is to provide an apparatus and method for vertebral body recognition in medical images, that creates a three-dimensional medical image and identifies a specific vertebral body from the three-dimensional medical image based on coronal projection information.

In addition, another object of the present disclosure is to provide an apparatus and method of identifying a vertebral body in medical images that identifies a specific vertebral body and assigns a number to the specific vertebral body to facilitate tissue composition analysis of the position of the specific vertebrae in follow-up examinations.

According to an aspect of the present disclosure, there is provided an apparatus of identifying a vertebral body from a medical image, the apparatus including a vertebral bone identification module configured to identify the vertebral body based on a multi-slice medical image provided from an outside, in which the vertebral identification module reconstructs the multi-slice medical image to create a three-dimensional medical image, obtains a coronal projection image for the three-dimensional medical image by projecting the three-dimensional medical image in a coronal plane direction, divides the coronal projection image into a selection area including at least one of lumbar and thoracic, obtains area information corresponding to the selection area in the three-dimensional medical image based on the divided selection area, and performs numbering on the vertebral body based on the area information and the three-dimensional medical image.

In the creation of the three-dimensional medical image, preprocessing for reducing a noise of the multi-slice medical image may be performed.

In the creation of the three-dimensional medical image, a slice image set may be created so that a slice thickness of the multi-slice medical image is the same as a pixel size within a slice, and the three-dimensional medical image may be created based on the slice image set.

A pre-trained deep learning models may be applied to the creation of the slice image set, and the deep learning model may output a larger number of slice images than the number of input multi-slice medical images.

The deep learning model may divide a slice included in the multi-slice medical image in a thickness direction and output a large number of slice images while a slice thickness is the same as a pixel size in the slice.

In the obtaining of the coronal projection image, the three-dimensional medical image may be projected at a maximum pixel intensity when projected in a coronal plane direction.

A pre-trained deep learning model may be applied to the division of the selection area, and the deep learning model may be operated to identify and divide the selected area from the coronal projected area.

The deep learning model may create a bounding box in the identification of the selection area.

A pre-trained deep learning model may be applied to the obtaining of the area information, and the deep learning model may be trained to obtain area information corresponding to the selection area from the three-dimensional medical image.

In the performing of the numbering on the vertebral body, the three-dimensional medical image is input into a pre-trained deep learning model to divide the vertebral body, and the numbering on the vertebral body may be performed based on the area information.

According another aspect of the present disclosure, there is provided method of identifying a vertebral body from a medical image, the method including: reconstructing a multi-slice medical image provided from an outside to create a three-dimensional medical image; obtaining a coronal projection image for the three-dimensional medical image by projecting the three-dimensional medical image in a coronal plane direction; dividing the coronal projection image into a selection area including at least one of a lumbar and a thoracic; obtaining area information corresponding to the selection area in the three-dimensional medical image based on the divided selection area; and performing numbering on the vertebral body based on the area information and the three-dimensional medical image.

In the creating of the three-dimensional medical image, preprocessing for reducing a noise of the multi-slice medical image is performed.

The creating of the three-dimensional medical image may include creating a slice image set so that a slice thickness of the multi-slice medical image is the same as a pixel size within a slice, and creating the three-dimensional medical image based on the slice image set.

A pre-trained deep learning models may be applied to the creating of the slice image set, and the deep learning model may output a larger number of slice images than the number of input multi-slice medical images.

The deep learning model divides a slice included in the multi-slice medical image in a thickness direction and outputs a large number of slice images while a slice thickness is the same as a pixel size in the slice.

In the obtaining of the coronal projection image, the three-dimensional medical image may be projected at a maximum pixel intensity when projected in a coronal plane direction.

A pre-trained deep learning model may be applied to the dividing of the selection area, and the deep learning model may be operated to identify and divide the selected area from the coronal projected area.

The deep learning model may create a bounding box in the identification of the selection area.

A pre-trained deep learning model may be applied to the obtaining of the area information, and the deep learning model may be trained to obtain area information corresponding to the selection area from the three-dimensional medical image.

The performing of the numbering on the vertebral body may include inputting the three-dimensional medical image into a pre-trained deep learning model to divide the vertebral body, and performing the numbering on the vertebral body based on the area information.

According to the apparatus and method for vertebral body recognition in medical images, of the present disclosure, it is possible to identify the vertebral body based on the coronal projection information, achieve more accurate identification performance, and realize more accurate tissue composition analysis in a follow-up examination based on the identified vertebral body.

The technical effects of the present disclosure as described above are not limited to the effects mentioned above, and other technical effects not mentioned may be clearly understood by those skilled in the art from the description below.

DESCRIPTION OF EXEMPLARY EMBODIMENTS

Figure 1:
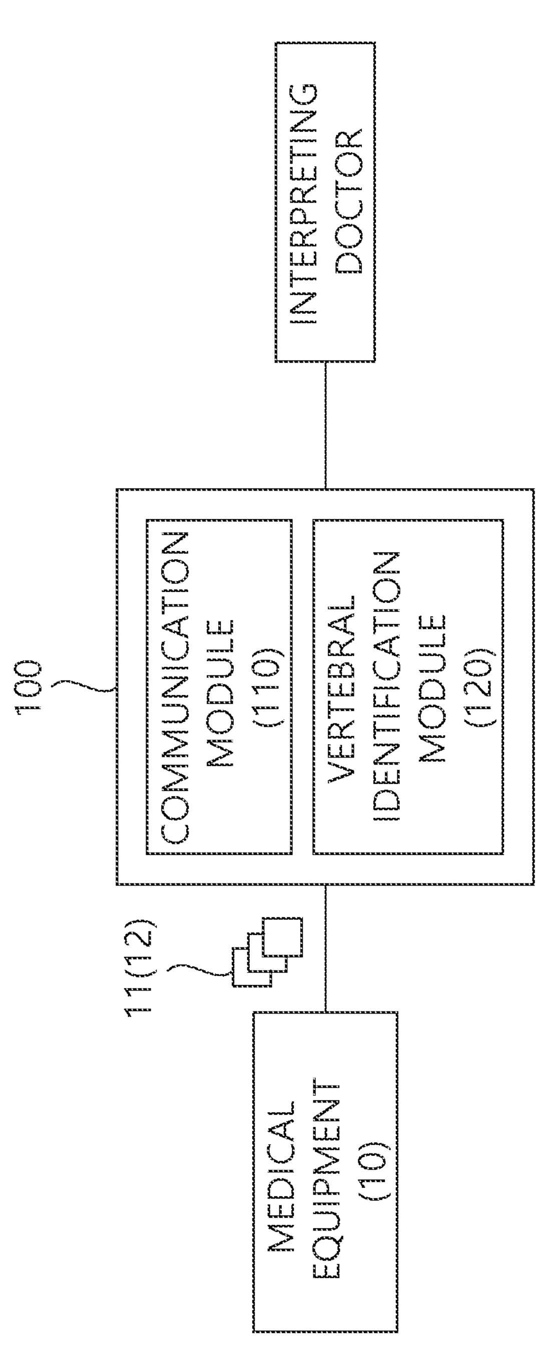
FIG. 1 is a schematic diagram illustrating a configuration of an apparatus of identifying a vertebral body in a medical image according to the present embodiment.

Hereinafter, an embodiment of present disclosure will be described in detail with reference to the attached drawings. However, the present embodiment is not limited to the embodiment disclosed below and can be implemented in various forms, and the present embodiment is provided to ensure that the present disclosure is complete and to fully inform those skilled in the art of the scope of the invention. The shapes of elements in the drawings may be exaggerated for clearer explanation, and elements indicated with the same symbol in the drawings refer to the same elements.

FIG. 1 is a schematic diagram illustrating a configuration of an apparatus of identifying a vertebral body in a medical image according to the present embodiment.

FIG. 1 illustrates that a vertebral body identification apparatus 100 (hereinafter, referred to as a vertebral body identification apparatus) of a medical image according to the present embodiment identifies a vertebral body from medical image data acquired from medical equipment 10. Moreover, the vertebral body identification apparatus 100 can distinguish the identified vertebrae, perform numbering on a lumbar area or a thoracic area, and deliver the results to an interpreting doctor.

However, hereinafter, a method of performing numbering in the lumbar area will be described to help understand the present disclosure. However, this is for the purpose of explaining the present embodiment, and the vertebral body identification apparatus 100 may perform the numbering on the lumbar area and/or the thoracic area.

In addition, the medical equipment 10 may be a computed tomography (CT), magnetic resonance imaging (MRI), and positron emission tomography (PET), or the like, but the medical equipment 10 and a type of the medical image are not limited.

This vertebral body identification apparatus 100 may include a communication module 110 and a vertebral identification module 120. Here, the communication module 110 and the vertebral identification module 120 may each be provided as independent components or may be built together in a single computer system.

First, the communication module 110 receives medical image data 11 that may be provided through the medical apparatus 100 or a server (not illustrated). Here, the medical image data 11 is image data taken of a spine area of a patient and may include a multi-slice medical image 12.

Moreover, the vertebral identification module 120 processes the multi-slice medical image 12 provided through the communication module 110 to identify the vertebral body. Additionally, the vertebral identification module 120 may perform numbering on a lumbar area of the identified vertebral body.

Hereinafter, a method of processing the vertebral identification module 120 will be described in detail with reference to the attached drawings. However, detailed description of the above-described components will be omitted and they will be described by assigning the same reference numerals.

Figure 2:
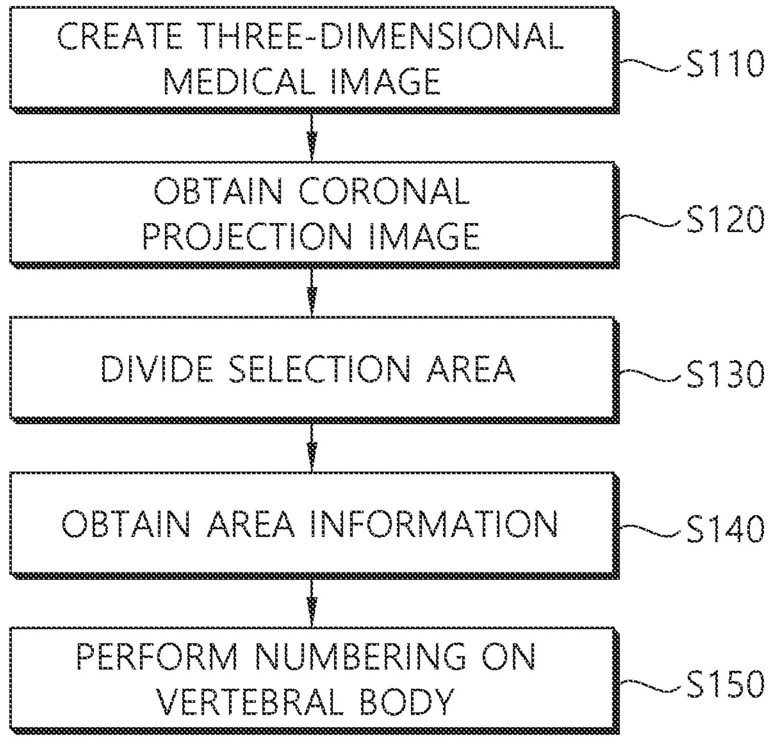
FIG. 2 is a flowchart illustrating a method of identifying a vertebral body in a medical image according to the present embodiment.
Figure 3:
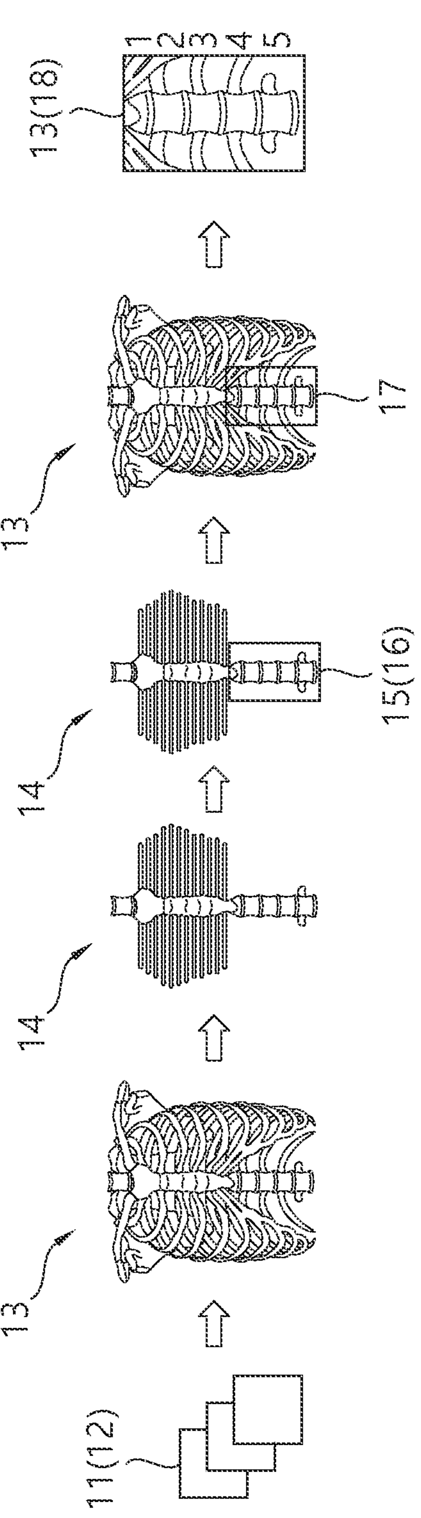
FIG. 3 is a conceptual diagram illustrating the method of identifying a vertebral body in a medical image according to the present embodiment.

FIG. 2 is a flowchart illustrating a method of identifying a vertebral body in a medical image according to the present embodiment, and FIG. 3 is a conceptual diagram illustrating the method for identifying a vertebral body in a medical image according to the present embodiment.

As illustrated in FIGS. 2 and 3, in the identifying of the vertebral body according to the present embodiment, the vertebral identification module 120 performs preprocessing on the multi-slice medical image 12 provided through the communication module 110 to create a three-dimensional medical image 13 (S110).

Here, the method of the vertebral identification module 120 performing the preprocessing on the multi-slice medical image 12 to create the three-dimensional medical image 13 may be implemented in various ways.

For example, the vertebral identification module 120 may remove a noise from the input multi-slice medical image 12, reconstruct the noise-removed multi-slice medical image 12, and create the three-dimensional medical image 13. In this case, the vertebral identification module 120 may remove the noise from the multi-slice medical image 12 and create the three-dimensional medical image 13 using a first pre-trained deep learning model.

For example, the first pre-trained deep learning model is a deep learning model trained to reduce the noise by pairing a multi-slice medical image including a low quality and a multi-slice medical image including a high quality.

As another example, the first pre-trained deep learning model may be a deep learning model trained by pairing a sinogram of a multi-slice medical image including a low quality and a sinogram of a multi-slice medical image including a high quality. In other words, the first deep learning model according to another example may perform noise reduction at the sinogram level.

As another example, the first pre-trained deep learning model may be a deep learning model trained by pairing a three-dimensional medical image including a low quality and a three-dimensional medical image including a high-quality. In other words, the first deep learning model according to another example may perform the noise reduction after creating the three-dimensional medical image.

In this way, the vertebral identification module 120 may perform the noise removal in a process of converting the multi-slice medical image 12 into the three-dimensional medical image 13 using the first pre-trained deep learning model. However, this is for explaining the present embodiment, various types of deep learning models may be applied to the noise reduction method performed in the process of creating the three-dimensional medical image 13, and the noise reduction method may be performed through the conventional image processing method without applying the deep learning model.

Meanwhile, the vertebral identification module 120 may create a slice image set so that a slice thickness of the multi-slice medical image 12 is the same as a pixel size within the slice to improve the image quality of the three-dimensional medical image 13 in the process of creating the three-dimensional medical image 13 from the multi-slice medical image 12, and reconstruct the three-dimensional medical image 13.

For example, the vertebral identification module 120 may apply a second pre-trained deep learning model. Here, the second deep learning model may be trained to output a larger number of slice images than the number of input multi-slice medical images 12.

For example, the second deep learning model may divide the slice included in the multi-slice medical image 12 in the thickness direction. Accordingly, the second deep learning model may output a large number of slices while the slice thickness is the same as the pixel size within the slice.

This second deep learning model may be a deep learning model trained by pairing a thin slice and a thick slice. Accordingly, when the slice is input, the second deep learning model may divide the slice in the thickness direction.

In this way, the vertebral identification module 120 may perform the preprocessing in various ways and convert the multi-slice medical image 12 into the three-dimensional medical image 13.

Meanwhile, when the three-dimensional medical image 13 is created, the vertebral identification module 120 projects the created three-dimensional medical image 13 as a coronal projection image 14 (S120). In this case, the vertebral identification module 120 may perform projection at maximum pixel intensity from the three-dimensional medical image 13 in a coronal plane direction.

Afterwards, the vertebral identification module 120 divides a selection area 15 in the coronal projection image 14 projected at the maximum pixel intensity (S130).

Here, the vertebral identification module 120 can distinguish the lumbar area into the selection area 15 to perform numbering on the lumbar area. Here, the vertebral identification module 120 may distinguish the lumbar area and/or the thoracic area, but as described above, for example, the lumbar area may be distinguished into the selection area 15.

In the distinguishing of selection area 15, a third pre-trained deep learning model may be applied.

For example, the third deep learning model may be trained by pairing the coronal projection image 14 and the medical image, such as the lumbar or thoracic image, for the selection area 15 included in the coronal projection image 14. Accordingly, when the coronal projection image 14 is input, the third deep learning model can distinguish the selection area 15 from the coronal projection image 14, and the lumbar area in the present embodiment. In this case, in the learning of the third deep learning model, the third deep learning model may be trained to distinguish the lumbar area based on the presence or absence of ribs in the process of distinguishing the lumbar area from the coronal projection image 14 of the vertebral body.

Additionally, the third deep learning model may create a bounding box 16 in the lumbar area in the process of distinguishing the lumbar area. In this case, the created bounding box 16 may be output to an operator through a display unit (not illustrated). Accordingly, the operator may check whether the lumbar area is accurately distinguished from the coronal projection image 14 through the bounding box 16.

For example, the lumbar area may include a total of 5 lumbar areas, from a 1st lumbar to a 5th lumbar. Accordingly, the third deep learning model may obtain the bounding box 16 including a series of lumbar areas starting from the 1st lumbar to the 5th lumbar in order to divide the lumbar area.

In addition, in the learning of this third deep learning model, the selection area 15 may be learned by dividing the selection area into the lumbar area and a disc area. Accordingly, the trained deep learning model considers the disc area and may distinguish the lumbar area.

Afterwards, the vertebral identification module 120 obtains the area information 17 corresponding to the lumbar area from the three-dimensional medical image 13 preprocessed based on the divided selection area 15.

For example, the vertebral identification module 120 can identify the area information 17 corresponding to the bounding box 16 in the three-dimensional medical image 13 preprocessed based on the obtained bounding box 16. Here, the vertebral identification module 120 may apply various methods to identify the area information 17 in the preprocessed three-dimensional medical image 13.

For example, the vertebral identification module 120 may identify the area information 17 from the three-dimensional medical image 13 based on a fourth pre-trained deep learning model.

As an example, the fourth deep learning model can be trained by pairing the image for the bounding box 16 and the three-dimensional medical image 13. Accordingly, the fourth deep learning model may output the area information 17 corresponding to the selection area 15 from the preprocessed three-dimensional medical image 13.

Thereafter, the vertebral identification module 120 may identify a specific vertebral body 18 based on the previously acquired area information 17 and the preprocessed three-dimensional medical image 13 and perform numbering.

For example, the vertebral identification module 120 inputs the preprocessed three-dimensional medical image 13 into a fifth pre-trained deep learning model to divide the vertebral body 18 of the preprocessed three-dimensional medical image 13.

For example, the fifth deep learning model can be trained by pairing the three-dimensional medical image 13 and the image of the vertebral body 18. Accordingly, the fifth deep learning model may identify the vertebral body 18 from the preprocessed three-dimensional medical image 13 and output the identified vertebral body 18.

Afterwards, the vertebral identification module 120 may perform numbering on the vertebral body 18 output from the preprocessed three-dimensional medical image 13 and the vertebral body 18 based on the area information 17.

In other words, the vertebral identification module 120 may compare the area information of the three-dimensional medical image 13 created from the lumbar area according to the coronal plane projection to the vertebral body 18, which is the result output from the three-dimensional medical image 13, and perform the numbering on the vertebral body 18 identified from the three-dimensional medical image 13.

In this way, according to the apparatus and method for vertebral body recognition in medical images, of the present disclosure, it is possible to identify the vertebral body based on the coronal projection information, achieve more accurate identification performance, and realize more accurate tissue composition analysis in a follow-up examination based on the identified vertebral body.

The embodiment of present disclosure described above and illustrated in the drawings should not be construed as limiting the technical idea of present disclosure. The scope of protection of present disclosure is limited only by the matters stated in claims, and a person with ordinary knowledge in the technical field of present disclosure can improve and change the technical idea of present disclosure into various forms. Therefore, these improvements and changes will fall within the scope of protection of present disclosure as long as they are obvious to a person with ordinary knowledge.

What is claimed is:

1. An apparatus of identifying a vertebral body from a medical image, the apparatus comprising:

a vertebral identification module configured to identify the vertebral body based on a multi-slice medical image, wherein the vertebral identification module reconstructs the multi-slice medical image to create a three-dimensional medical image, obtains a coronal projection image for the three-dimensional medical image by projecting the three-dimensional medical image in a coronal plane direction, divides the coronal projection image into a selection area including at least one of lumbar and thoracic, obtains area information corresponding to the selection area in the three-dimensional medical image based on the divided selection area, and performs numbering on the vertebral body based on the area information and the three-dimensional medical image, and wherein in the performing of the numbering on the vertebral body, the three-dimensional medical image is input into a pre-trained deep learning model to divide the vertebral body, and the numbering on the vertebral body is performed based on the area information.

2. The apparatus of claim 1, wherein in the creation of the three-dimensional medical image, preprocessing for reducing a noise of the multi-slice medical image is performed.

3. The apparatus of claim 1, wherein in the creation of the three-dimensional medical image, a slice image set is created so that a slice thickness of the multi-slice medical image is the same as a pixel size within a slice, and the three-dimensional medical image is created based on the slice image set.

4. The apparatus of claim 3, wherein a pre-trained deep learning models is applied to the creation of the slice image set, and the deep learning model outputs a larger number of slice images than the number of input multi-slice medical images.

5. The apparatus of claim 3, wherein the deep learning model divides a slice included in the multi-slice medical image in a thickness direction and outputs a large number of slice images while a slice thickness is the same as a pixel size in the slice.

6. The apparatus of claim 1, wherein in the obtaining of the coronal projection image, the three-dimensional medical image is projected at a maximum pixel intensity when projected in a coronal plane direction.

7. The apparatus of claim 1, wherein a pre-trained deep learning model is applied to the division of the selection area, and the deep learning model is operated to identify and divide the selected area from the coronal projected area.

8. The apparatus of claim 7, wherein the deep learning model creates a bounding box in the identification of the selection area.

9. The apparatus of claim 1, wherein a pre-trained deep learning model is applied to the obtaining of the area information, and the deep learning model is trained to obtain area information corresponding to the selection area from the three-dimensional medical image.

10. A method of identifying a vertebral body from a medical image, the method comprising:

reconstructing a multi-slice medical image to create a three-dimensional medical image;

obtaining a coronal projection image for the three-dimensional medical image by projecting the three-dimensional medical image in a coronal plane direction;

dividing the coronal projection image into a selection area including at least one of a lumbar and a thoracic;

obtaining area information corresponding to the selection area in the three-dimensional medical image based on the divided selection area; and performing numbering on the vertebral body based on the area information and the three-dimensional medical image, wherein the performing of the numbering on the vertebral body includes:

inputting the three-dimensional medical image into a pre-trained deep learning model to divide the vertebral body; and performing the numbering on the vertebral body based on the area information.

11. The method of claim 10, wherein in the creating of the three-dimensional medical image, preprocessing for reducing a noise of the multi-slice medical image is performed.

12. The method of claim 10, wherein the creating of the three-dimensional medical image includes creating a slice image set so that a slice thickness of the multi-slice medical image is the same as a pixel size within a slice, and creating the three-dimensional medical image based on the slice image set.

13. The method of claim 12, wherein a pre-trained deep learning models is applied to the creating of the slice image set, and the deep learning model outputs a larger number of slice images than the number of input multi-slice medical images.

14. The method of claim 12, wherein the deep learning model divides a slice included in the multi-slice medical image in a thickness direction and outputs a large number of slice images while a slice thickness is the same as a pixel size in the slice.

15. The method of claim 10, wherein in the obtaining of the coronal projection image, the three-dimensional medical image is projected at a maximum pixel intensity when projected in a coronal plane direction.

16. The method of claim 10, wherein a pre-trained deep learning model is applied to the dividing of the selection area, and the deep learning model is operated to identify and divide the selected area from the coronal projected area.

17. The method of claim 16, wherein the deep learning model creates a bounding box in the identification of the selection area.

18. The method of claim 10, wherein a pre-trained deep learning model is applied to the obtaining of the area information, and the deep learning model is trained to obtain area information corresponding to the selection area from the three-dimensional medical image.

* * * * *